United States Patent [19]

Collins et al.

[11] Patent Number: 4,536,592

[45] Date of Patent: Aug. 20, 1985

[54] 2-SUBSTITUTED PROSTAGLANDINS

[75] Inventors: Paul W. Collins, Deerfield; Alan F. Gasiecki, Vernon Hills; Richard M. Weier, Lake Bluff, all of Ill.

[73] Assignee: G. D. Searle & Co., Skokie, Ill.

[21] Appl. No.: 580,966

[22] Filed: Feb. 16, 1984

[51] Int. Cl.$^3$ .............................................. C07C 177/00
[52] U.S. Cl. ....................................... 560/53; 560/118; 560/121; 562/463; 562/500; 562/503
[58] Field of Search ......................... 560/121, 53, 118; 562/503, 463, 500

[56] References Cited

U.S. PATENT DOCUMENTS 4,452,994  6/1984  Hill ...................................... 560/121

Primary Examiner—Robert Gerstl
Attorney, Agent, or Firm—John J. McDonnell

[57] ABSTRACT

The present invention encompasses 16-alkyl, 16-hydroxy-2-substituted prostaglandins which exhibit cytoprotective and antisecretory activity with greatly reduced diarrhea side effects.

6 Claims, No Drawings

2-SUBSTITUTED PROSTAGLANDINS

BACKGROUND OF THE INVENTION

U.S. Pat. Nos. 3,965,143; 4,087,621; 4,060,691 and 4,322,543 extensively disclose 16 alkyl, 16 hydroxy prostaglandins. Compounds of the present invention structurally differ from the prior art compounds by substitution at the 2 position. For example, the prior art discloses

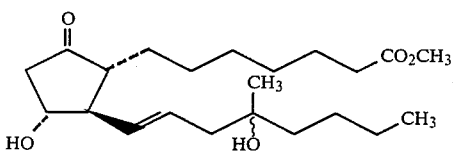

and the most closely related compound of the claimed invention is

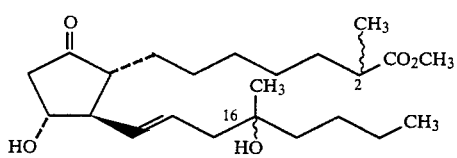

differing only by the methyl group at the 2 position. This slight change in structure dramatically alters the biological properties of the molecule.

Various 2-substituted prostaglandins are described in Recl. Trav. Chim. Pays-Bas 94(12), 247–256 (1975) (fluoro, bromo, phenyl); U.S. Pat. No. 3,874,966 (fluoro, methyl); J. Lipid Research 17(4), 424–30 (1976) (methyl).

SUMMARY OF THE INVENTION

This invention encompasses compounds of the formula

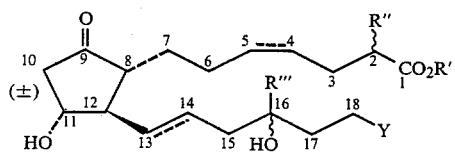

wherein the dotted lines represent optional double bonds cis at C-4,5 and trans at C-13,14 and the wavy lines represent optional R,S stereochemistry; wherein R' represents hydrogen or lower alkyl having 1 to 6 carbon atoms; R" represents lower alkyl containing 1 to 6 carbon atoms, alkenyl or alkynyl containing 2–6 carbon atoms; cycloalkyl containing 5 to 7 carbon atoms, halo or an aromatic radical of the formula —(CH$_2$)$_m$—AR wherein m is 0 to 3 and Ar represents phenyl or pyridyl optionally substituted with halo, lower alkyl containing 1 to 6 carbon atoms, trifluoromethyl or lower alkoxy containing 1 to 3 carbon atoms; R''' represents hydrogen, lower alkyl containing 1 to 6 carbon atoms, vinyl, ethynyl; and Y represents a straight or branched chain lower alkyl containing 1 to 4 carbon atoms or cyclopropyl.

These compounds are cytoprotective and antisecretory agents with significantly reduced diarrheogenic activity.

DETAILED DESCRIPTION OF THE INVENTION

More particularly considering the compounds of formula III the dotted lines may each be saturated or unsaturated and either one may be unsaturated while the other is saturated, however the cis configuration is maintained at the C-4,5 double when present and the trans configuration is maintained at the C-13,14 positions when present. Synthetic methods for building prostaglandin nuclei which are saturated and unsaturated at C-4,5 [J. Med. Chem., 26 (6), 786 (1983)] or C-13,14 are well known.

It is further known how to prepare these prostaglandin nuclei with C-16 substitution of hydroxy and R''' as lower alkyl containing 1–6 carbon atoms such as methyl, ethyl, propyl, isopropyl, butyl, pentyl, and hexyl as well as unsaturated radicals such as vinyl, ethynyl.

Methods for modifying the Y portion of formula III are also well known and various straight and branched chain lower alkyls containing 1–4 carbon atoms such as methyl, ethyl, propyl, isopropyl, and butyl are readily prepared.

The primary structural distinction of compounds encompassed by this invention is the substitution of R" at C-2. R" may be a wide variety of substituents. It may be lower alkyl containing 1–6 carbon atoms illustrated by methyl, ethyl, propyl, isopropyl, butyl, pentyl, hexyl; cycloalkyl containing 5 to 7 carbon atoms such as cyclopentyl, cyclohexyl, and cycloheptyl, unsaturated radicals such as vinyl, ethynyl, propargyl, allyl; or a large variety of aromatic radicals of the formula —(CH$_2$)$_m$—Ar wherein m is 0–3 and Ar is phenyl or pyridyl variously substituted. Thus phenyl, benzyl, phenethyl, phenpropyl, or pyridylmethyl substituted with lower alkyl such as methyl, ethyl; halo such as trifluoromethyl, fluoro, chloro, bromo, iodo; methoxy, ethoxy, and the like are contemplated by the invention. The preferred compounds are prepared by the following reaction scheme:

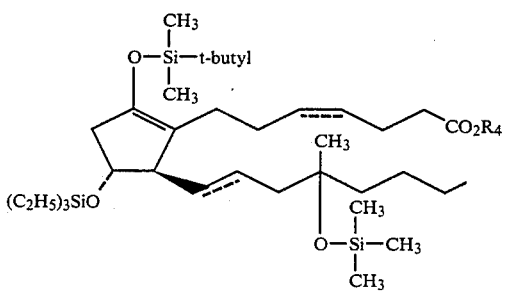

1. | n-butyl lithium/cyclohexyl isopropyl amine
   | $R_4I$

2. | dilute acid

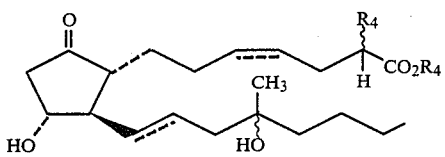

wherein $R_4$ represents the same or different lower alkyl containing 1-6 carbon atoms and the dotted lines represent optional double bonds which are cis at C-4,5 and trans at C-13,14. Other R" I or R" Br can be conveniently used to prepare the corresponding R" substitution at C-2.

The cytoprotective utility of compounds of this invention are illustrated by a standard test which shows their ability to reduce ethanol-induced gastric lesions.

0.5 mg/kg of the test compound is orally administered to adult 180–220 gram Charles River rats which have been deprived of food for 24 hours. Thirty minutes later 1.0 ml of absolute ethanol is administered intragastrically. The rats are sacrificed sixty minutes after alcohol administration and the gastric mucosae are visually examined for the presence of lesions. The number and severity of lesions are scored. A compound is judged active if it provides a statistically signficant reduction in the number and/or severity of lesions compared to the control group.

The standard test used to detect gastric anti-secretory activity is described as follows.

Adult female beagle dogs weighing 13–20 kg. are prepared with denervated fundic Heidenhain pouches. After a recovery period of at least 4 weeks following surgery, the animals are fasted for approximately 20 hours, then are placed in Pavlov stands and infused intravenously with saline solutions. The pouched secretions are collected every 15 minutes and measured for volume and total acidity by titration with 0.1N sodium hydroxide to pH 7.0. Following a 30 minute basal secretion the dogs are infused with a saline solution of histamine dihydrochloride at a dose of 1.0 mg./hr. A steady state plateau of gastric secretion is obtained approximately 1 hour following the start of histamine infusion, at the end of which time the test compound dissolved in an ethanolic iso-osmotic phosphate buffer solution, is administered by a single intraveneous injection. The duration of the anti-secretory effects is determined and the side-effects, if any, recorded. The compound is rated active if statistically significant inhibition of secretory parameters occur following compound treatment.

Diarrhea is an undesirable side effect commonly associated with prostaglandins. Diarrheogenic activity is demonstrated by the following standardized test.

Groups of six adult male Charles River rats, weight range 180 to 200 grams are fasted for 24 hours prior to administering the test substance. The prostaglandin to be tested is administered intragastrically in iso-osmotic phosphate buffer at a volume of 10 ml/kg at doses ranging from 100 to 3000 microgram/kg. Control animals receive only the vehicle. The rats are placed in individual wire mesh cages and the trays lined with brown paper. Diarrhea is assessed at hourly intervals on an all or none basis for up to eight hours after administration of the prostaglandin. Diarrhea is defined as any loose or watery stool. $ED_{50}$ value is assessed for each hourly diarrheogenic response.

Thus compounds of this invention are useful as cytoprotective agents with reduced diarrhea side effects. They have antiulcer ability as well as cytoprotective effects extending to other organs such as the pancreas and liver and large and small intestine.

Illustrative of the diarrheogenic properties of compounds of this invention are:

|  | Rat 8 hour Diarrheogenic $ED_{50}$ μg/kg |
|---|---|
| Compound I | 366 |
| Compound II | >3200 |

The diarrheogenic side effects are thus greatly reduced.

Regardless of the route of administration selected, the novel compounds of the invention are formulated into pharmaceutically acceptable dosage forms by conventional methods known to the pharmaceutical art.

The compounds can be administered in such oral unit dosage forms as tablets, capsules, pills, powders, or granules. They also may be administered intraperitoneally, subcutaneously, or intramuscularly, using forms known to the pharmaceutical art. In general, the preferred form of administration is oral. An effective but non-toxic quantity of the compound is employed in treatment. The dosage regimen for cytoprotection by the compounds of this invention is selected in accordance with a variety of factors including the type, age, weight, sex, and medical condition of the patient, the organ to be protected, the route of administration and the particular compound employed. An ordinarily skilled physician will readily determine and prescribe the effective amount of the cytoprotective agent required to prevent or arrest the progress of the condition. In so proceeding, the physician could employ relatively low dosages at first, subsequently increasing the dose until a maximum response is obtained. Dosages of the compounds of the invention are ordinarily in the area of 0.01 to 10,000 μg/kg. The compounds of this invention are used to treat diseases resulting from cellular problems in major systems such as the digestive system, liver, pancrease, urinary tract, respiratory system, cardiovascular system, and immunological system. They are used, for example, to treat liver disease resulting from alcohol abuse, cirrhosis of the liver, hepatitis, portal hypertension, hepatic tuberculosis and neoplasms. They are used to treat cardiac, cerebral or other organ cellular damage due to ischemia, pancreatitis, bileary dyskinesia, diabetic nephropathy, cystitis, urethritis, obstructive lung disease, pneumonia, rhinitis, laryngitis, asthma, endocarditus, reflux esophagitis, cerebral embolism, hemorrhage, blood platelet disorders, Addison's disease, poisoning by cadmium, lead and mercury and carbon tetrachloride.

The invention is more fully described in the following examples. The examples are not intended to limit the invention in spirit or scope.

EXAMPLE 1

2.12 Part of 4(RS)-4-trimethylsilyloxy-4-methyl-1-octyne and 3 parts of tri-n-butyltin hydride are mixed and irradiated under argon with a sun lamp at 0° C. for 2 hours and then at 55° for 2 hours to provide trans-1-tri-n-butylstannyl-4(RS)-4-trimethylsilyloxy-4-methyl-1-octene.

10 Parts of this trans vinyl tin product is dissolved in 25 parts by volume of tetrahydrofuran, cooled to −60° C. and 12.8 parts by volume of 1.66 molar butyl lithium is added while maintaining the reaction mixture in an argon atmosphere. After 1 hour at −60° C. a solution of 2.62 parts of copper penthye and 6.4 parts of hexamethylphosphorous triamide in 25 parts by volume of ether are added. After 10 minutes a solution of 3.55 parts of 7-(3-triethysilyloxy-5-oxocyclopent-1-ene)heptanoate in 25 parts by volume of ether are slowly added. After 30 minutes 3 parts of t-butyldimethylsilyl chloride and 25 parts by volume of hexamethylphosphoric triamide are added and the mixture is slowly warmed to 0° C., diluted with ether and hexane and washed 2 times with 1N hydrochloric acid and three times with water. The ether layer is separated, dried with sodium sulfate and the ether is removed by evaporation under reduced pressure.

The mixture is chromotographed on silica gel and eluted in 2% ethyl acetate in hexane to provide methyl 7-[3-triethylsilyloxy-2β-(4(RS)-4-trimethylsilyloxy-4-methyl-1-trans-octenyl)-5-tertiarybutyl dimethysilyloxycylopent-1-(5)-ene]-1α-heptanoate, having the formula

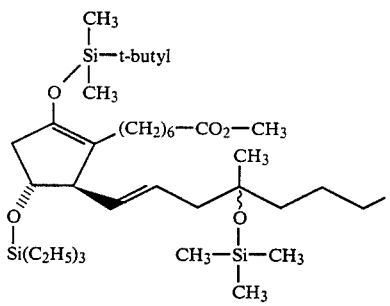

0.184 parts of cyclohexylisopropylamine are dissolved in 6 parts by volume of tetrahydrofuran and the solution is cooled to −60° C. and placed under argon prior to adding 0.8 parts by volume of 1.66 molar n-butyllithium slowly. After 1 hour, solution of 0.683 parts of the prostaglandin product above in 13 parts by volume of tetrahydrofuran is added over 1 hour, then a solution of 0.227 parts of iodemethane in 3 parts by volume of tetrahydrofuran is added rapidly to provide the 2-methyl derivative of the above compound.

This compound is treated with 3 parts of a 3:1:1 acetic acid:water:tetrahydrofuran mixture to which is then added a trace of 1N hydrochloric acid solution. The mixture is warmed in a water bath at 55° C. for 1 hour, cooled to room temperature, diluted with ether, washed 4 times with water, dried over sodium sulfate and evaporated under reduced pressure. The residue is chromatographed on silica gel and eluted with 75% ethyl acetate/25% hexane to provide methyl 7-[3α-hydroxy-2β-4-hydroxy-4-methyl-1-trans-octenyl)-5-oxocyclopentane]-1α-2-methyl-heptanoate having the formula

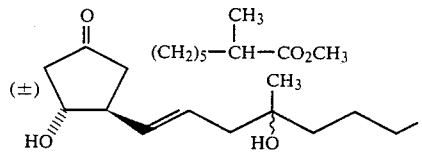

viscous colorless oil, $H^1$ NMR (CDCl3): 1.13δ (doublet, J=7 C-2 methyl group); 1.18δ (singlet 16-$CH_3$); 3.66δ (singlet, ester); δ4.02 (quartet, C-11); 5.35δ dd, J=16,8 (C-13); 5.7δ, J=16,7 (C-14).

EXAMPLE 2

Following the procedure of Example 1 replacing the iodomethane with iodoethane provides methyl 7-[3α-hydroxy-2β-4(RS)-4-hydroxy-4-methyl-1-trans-octenyl)-5-oxocyclopentane]-1α-2-ethyl-heptanoate.

$H^1$NMR: δ0.87, triplet, J=7 ($CH_3$ of ethyl group at C-2); 3.65δ (singlet); δ4.02, q (C-11).

EXAMPLE 3

Following the procedure of Example 1 replacing the iodomethane with isopropyl iodide provides methyl 7-[3α-hydroxy-2β-4(RS)-4-hydroxy-4-methyl-1-trans-octenyl)-5-oxocyclopentane]-1α-2-isopropyl-heptanoate, a viscous oil.

$H^1$ NMR: δ0.87, d; δ0.89, d; δ0.90 t; δ2.20, d, J=7.

EXAMPLE 4

Following the procedures of Example 1 replacing the iodomethane with allyl bromide provides methyl 7-[3α-hydroxy-2β-4(RS)-4-hydroxy-4-methyl-1-trans-octenyl)-5-oxocyclopentane]-1α-2-allyl heptanoate, a viscous oil.

$H^1$ NMR: δ1.15 s; δ3.64 s; 4.01 q.

EXAMPLE 5

Following the procedure of Example 1 replacing the iodomethane with benzyl bromide provides methyl 7-[3α-hydroxy-2β-4(RS)-4-hydroxy-4-methyl-1-trans-octenyl)-5-oxocyclopentane]-1α-2-benzyl heptanoate, a viscous oil.

$H^1$ NMR: δ3.62 s; δ7.15 m, aromatic protons. Halo, lower alkyl and lower alkoxy substituted benzyl and pyridylmethyl are made by substantially the same procedure.

EXAMPLE 6

Following the procedure of Example 1 replacing the iodomethane with cyclopentyl iodide provides methyl 7-[3α-hydroxy-2β-4(RS)-4-hydroxy-4-methyl-1-trans-octenyl)-5-oxocyclopentane]-1α-2-cyclopentyl heptanoate, a viscous oil.

$H^1$ NMR: δ1.17 s; δ3.65 s; δ4.03, q.

EXAMPLE 7

Using the procedure of Example 1 replacing the iodomethane with iodine provides methyl 7-[3α-hydroxy-2β-4(RS)-4-hydroxy-4-methyl-1-trans-octenyl)-5-oxocyclopentane]-1α-2-iodo heptanoate.

Viscous oil, $H^1$ NMR: δ1.18 s; δ3.73 s, methyl ester; δ4.02, q, C-11; δ4.27, t C-2 H.

EXAMPLE 8

24.1 parts of 5-chloro-2-pentanone in 200 parts by volume of tetrahydrofuran distilled from lithium aluminum hydride is added dropwise 88 parts by volume of 2.5 molar n-butyl lithium in hexane the reaction is conducted under argon at −65° C. The reaction mixture is slowly warmed to room temperature and poured into an ether/water mixture. The organic layer is separated, washed twice with water, and dried over anhydrous sodium sulfate. The solvent is evaporated under reduced pressure to provide 1-chloro-4-methyl-4-octanol.

25.1 parts of this material and 11.8 parts imidazole are dissolved in 250 parts by volume of dimethylformamide and then 15.3 parts of trimethylchlorosilane are added with stirring. After about 1 hour the reaction mixture is poured into hexane and water. The organic layer is separated, washed three times with water, dried over sodium sulfate, and evaporated under reduced pressure. The crude residue was separated by chromotography on silica gel with elution in 99% hexane and 1% ethyl acetate to provide 1-chloro-4-trimethylsilyloxy-4-methyl-octane.

6.25 parts of this material was mixed with 9.0 parts of lithium bromide and 2.65 parts by volume of diisopropylethylamine in 50 parts by volume of tetrahydrofuran and refluxed for 72 hours. Isolation of the reaction mixture as above followed by chromatography on silica gel with 100% hexane as the eluent to provide 1-bromo-4-trimethylsilyloxy-4-methyl-octane.

0.1 parts of magnesium turnings in 5 parts by volume of ether are treated with a trace of mercuric chloride and iodine to activate the magnesium. 0.89 parts of 1-bromo-4-trimethylsilyloxy-4-methyl-octane in 10 parts by volume of ether are added slowly to the activated magnesium. After the addition is completed, the reaction mixture is refluxed for 3 hours and then cooled to −20° C. prior to adding 0.4 parts of copper pentyne solubilized with 1.1 part of hexamethylphosphorous triamide in 5 parts by volume of ether. To this resulting mixture is added 0.5 parts of methyl 7-(3-triethylsilyloxy-5-oxocyclopent-1-ene)-hept-4-cis-enoate (described in U.S. Pat. No. 4,271,314) in 5 parts by volume of ether. After stirring for 30 minutes at −20° C., a solution of t-butyldimethylsilyl chloride in 2 parts by volume of ether is added and followed by adding 1.1 part of hexamethylphosphoric triamide. The mixture is stirred for 2 hours at −20° C. and stored overnight a −10° C. to −20° C. The mixture is poured into concentrated ammonium chloride solution and extracted with a mixture of hexane and ether. The organic layer is washed with 1N hydrochloric acid, saturated sodium chloride, and sodium bicarbonate. The ether layer is separated and dried over anhydrous sodium sulfate. The ether is evaporated under reduced pressure and the residual oil is chromatographed on silica gel with 1% ethyl acetate in hexane to provide methyl 7-[3α-triethylsilyloxy-2β-(4(RS)-4-trimethylsilyloxy-4-methyloctane)-5-tertiary-butyldimethylsilyloxycyclopent-1(5)ene]-1α-hept-4-cis-enoate having the formula

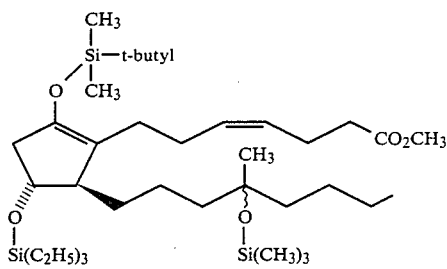

Using the same reagents and procedures as in Example 1 this compound is converted to methyl-7-[3α-hydroxy-2β-4(RS)-4-hydroxy-4-methyl-octan-5-oxocyclopentane]-1α-hept-2-methyl-4-cis-enoate having the formula

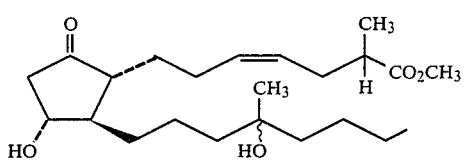

Viscous oil, H$^1$ NMR: δ1.14, d, C-2 methyl group; δ4.15, m, C-11; δ5.36, m C-4,5.

EXAMPLE 9

Starting with 7-(3-triethylsilyloxy-5-oxocyclopent-1-ene) heptanoate described in Example 1 and following the addition and alkylation procedure of Example 8 and using equivalent quantities provides methyl 7-[3α-hydroxy-2β-4(RS)-4-hydroxy-4-methyl-octan-5-oxocyclopentane] -1α-2-methyl heptanoate having the formula

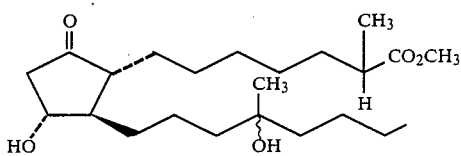

Viscous oil, H$^1$ NMR: δ1.13, d, C-2 methyl group; δ4.15, m, C-11; δ3.65, s, ester.

EXAMPLE 10

Hydrogenation of the product of Example 2 in isopropanol at room temperature and atmospheric pressure with 5% palladium on carbon as catalyst provides methyl 7-[3α-hydroxy-2β-4(RS)-4-hydroxy-4-methyl-octan-5-oxocyclopentane]-1α-2-ethyl heptanoate, having the formula

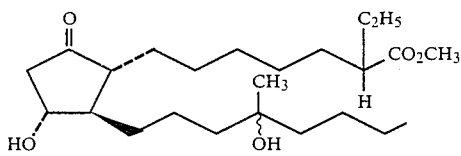

Viscous oil, H$^1$ NMR: δ0.87, t, (CH$_3$ of ethyl group at C-2); δ4.15, m, C-11.

EXAMPLE 11

Starting with methyl-7-[3-triethylsilyloxy-5-oxocyclopent-1-ene)hept-4-cis-enoate and following the addition procedure of Example 1 using equivalent quantities provides methyl-7[3α-hydroxy-2β-4-hydroxy-4-methyl-1-trans-octenyl)-5-oxocyclopentane]-1α-2-methyl-hept-4-cis-enoate having the formula

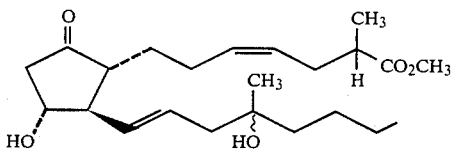

Viscous oil; H$^1$ NMR: δ1.12, d, C-2-methyl; δ3.65 methyl ester; δ4.02, m, C-11.

EXAMPLE 12

A solution of 33.25 parts of 3-butyn-1-ol in 500 parts by volume ether is cooled to −60° C. under argon and treated dropwise with 400 parts by volume of a 2.5 molar solution of n-butyl lithium in hexane. One hour after the addition is complete, a solution of 130 parts by volume of trimethylchlorosilane in 130 parts by volume of ether is added dropwise. After the addition is complete, the temperature is allowed to rise to 0°. The reaction mixture is poured into water, washed with 1NHCl 3 times, additional water, dried over sodium sulfate and evaporated to a liquid which is distilled under water aspirator pressure to give 4-trimethylsilyl-3-butyn-1-ol, bp. 75–77 (13 Tor).

A solution of 4.26 parts of the product above and 6.07 parts of triethylamine in 30 parts by volume of tetrahydrofuran is cooled to 0° and treated dropwise with 5.17 parts of methane sulfonyl chloride. After the addition is complete, the solution is filtered and evaporated. The residue is dissolved in 60 parts by volume of acetone and treated with 3.81 parts of lithium bromide. The solution is stirred at room temperature for 2 hours and refluxed for 3 hours. The solution is then cooled, and evaporated. The residue is taken up in ether and washed with dilute sodium bicarbonate solution and then water, dried over sodium sulfate and evaporated. The residual liquid is distilled under water aspirator pressure to give 4-trimethylsilyl-3-butyn-1-bromide, bp. 68°–70° (17 Tor).

A solution of the above bromide (3.08 parts) in 10 parts by volume of diethyl ether is added to a slurry of 0.5 parts of iodine-activated magnesium powder and 0.01 parts of mercuric chloride in 10 parts of ether. The rate of addition is adjusted to maintain a vigorous reflux. After addition is complete, the reaction mixture is stirred at room temperature for one hour and then cooled to 0°. A solution of 1.44 parts of 2-furancarboxaldehyde in 5 parts of diethyl ether is added dropwise, and the reaction mixture is stirred at room temperature for fifteen minutes, then poured onto a cold saturated ammonium chloride solution and stirred vigorously. The layers are separated and the aqueous layer is extracted with ether. The organic phase is washed with saturated ammonium chloride solution with brine, dried over sodium sulfate, filtered, and concentrated to dryness. Chromatography of the crude material on silica gel with 10% ethyl acetate/90% hexane as eluent gave 1.25 parts of 1-(4-trimethylsilyl-3-butyn)-2-furanyl methanol, as an oil. Structure assignment is confirmed by the proton nmr spectrum.

To a solution of 11.9 parts of the above compound in 180 parts by volume of a 8:1 dioxane/water mixture is added 0.725 parts of p-toluenesulfonic acid. The reaction mixture is heated at 83° for 36 hours under argon, cooled, and diluted with 500 ml of ethyl acetate. The organic phase is washed once with water and two times each with 5% sodium bicarbonate solution and brine solution. The aqueous washes are combined and extracted with ethyl acetate. The combined organic phases are dried over sodium sulfate, filtered, and concentrated. Chromatography of the combined crude materials on silica gel (using 10% ethyl acetate in hexane as eluent) give 4.72 parts of the intermediate compound 4-hydroxy-5-(1-trimethylsilyl-4-butynyl)-2-cyclopenten-1-one as a viscous oil. Structure assignment is confirmed by the proton nmr spectrum.

A solution of 4.72 parts of the cyclopentenone intermediate in 25 parts of ether is poured into a column packed with 95 parts of grade III alumnina (6% water by weight). The column is closed and allowed to stand at room temperature for twenty four hours. The product is eluted from the column with ether and ethyl acetate to give 4.4 parts of a viscous oil. This material is dissolved in dimethylformamide (75 parts by volume) and water (5 parts by volume) and treated with 5.0 parts of potassium fluoride. The solution is stirred overnight at room temperature, diluted with ether/ethyl acetate, washed with water twice, dried over sodium sulfate and evaporated. The residual oil is used without purification in the next step.

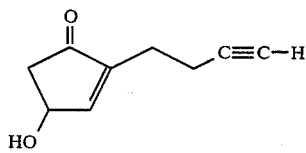

A solution of 0.250 parts of the above compound in 4 parts by volume of dimethylformamide is treated successively with 0.200 parts of imidazole and 0.300 parts of triethylsilyl chloride. After stirring for thirty minutes, the reaction mixture is diluted with ether, washed with water, dried over sodium sulfate, filtered, and concentrated to dryness. The crude material is chromatographed on silica gel to give 0.37 parts of 2-(4-butynyl)-4-[(triethylsilyloxy]-2-cyclopenten-1-one as an oil. Structure assignment is confirmed by the proton nmr spectrum.

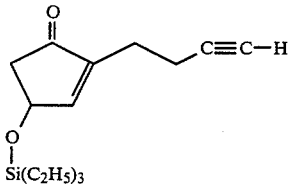

A solution of 10 parts trans-1-tri-n-butylstannyl-4(RS)-4-trimethylsilyloxy-4-methyl-1-octene of Example 1 in 25 parts by volume of tetrahydrofuran is cooled to −60° under an argon atmosphere, and 11.8 parts by volume of a 1.7M solution of n-butyllithium in hexane (0.02 mole) is added. The reaction mixture is stirred for forty five minutes, after which a solution of 2.62 parts of copper-1-pentyne and 6.4 parts of hexamethylphosphorus triamide in 75 parts by volume of ether is added dropwise. After ten minutes, a solution of 2.4 parts of the compound from the previous reaction in 20 parts by volume of ether is added, and the reaction mixture is stirred an additional 45 minutes. A solution of 3 parts of t-butyldimethylsilyl chloride in 15 parts by volume of ether is added, followed by the addition of 25 parts by volume of hexamethylphosphoric triamide. The temperature is allowed to rise to −20°, where it is maintained for one hour. The reaction mixture is poured into 1N hydrochloric acid and ether. The layers are separated and the organic phase is washed with water, dried over sodium sulfate, filtered, and concentrated to dryness. The crude material is chromatographed on silica gel to give 4 g of (1,1-dimethylethyl)dimethyl[[3β-[4-methyl-4-[(trimethylsilyl)oxy]-1E-octenyl]-2-(1-butynyl)-4α-[(triethylsilyl)oxy]-1-cyclopenten-1-yl]oxy]silane as a viscous oil. Structure is confirmed by the proton nmr spectrum.

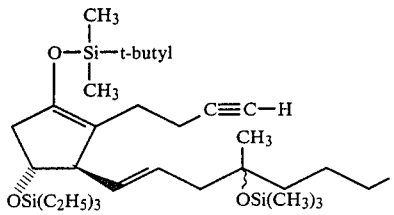

0.592 parts of this intermediate in 8 parts by volume of tetrahydrofuran is reacted with 0.9 parts by volume of 1.66 molar n-butyllithium at −30°−−20° for about 1 hour. Then a solution of 0.1 parts by volume of dimethylformamide in 2 parts by volume of tetrahydrofuran is added to provide an intermediate of the structure

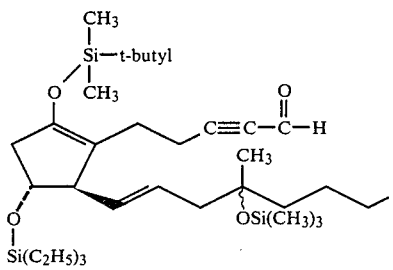

0.096 parts of sodium hydride in 2 parts by volume of tetrahydrofuran is reacted with 0.564 parts ethyl diethoxyphosphonofluoroacetate. The reaction mixture is treated with 0.60 parts of the prostaglandin intermediate above in 2 parts by volume of tetrahydrofuran. The reaction mixture is refluxed for about 1 hour, cooled and diluted with 20 parts by volume of hexane ether mixture and then washed with water, and dried over sodium sulfate and the solvent is removed by evaporation at reduced pressure. The mixture is chromatographed in 5% ethyl acetate/hexane to provide an intermediate of the structure

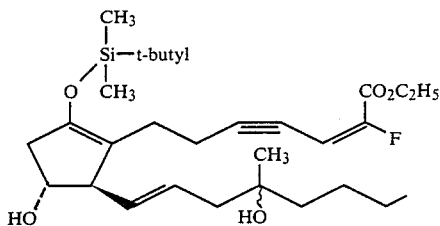

0.5 parts of this intermediate is reacted with 5 parts by volume of a 3:1:1 acetic acid/water/tetrahydrofuran mixture and then is reduced with hydrogen over palladium/BaSO4 catalyst at atmospheric pressure and room temperature to provide ethyl 7-[3α-hydroxy-2β-4-(RS)-4-hydroxy-4-methyl-1-trans-octenyl)-5-oxocyclopentane]-α-2-fluoro-heptanoate as a viscous oil having the formula

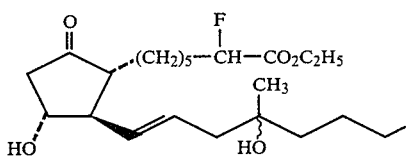

H¹ NMR: δ1.16, s, δ2.21, J=7, C-15; δ3.72, q J=8, CH2 of ethyl ester; δ4.01, q, J-8, C-11, δ4.83, dt, J=48,5; C-2 hydrogen.

EXAMPLE 13

4.9 parts of 5-hexen-2-one is dissolved in 357 parts by volume of benzene under argon and 75 parts by volume of a 25% solution of diethyl zinc is added dropwise over 15 minutes. 40 parts of diiodomethane in 500 parts by volume of benzene is added over 15 minutes. After sitting for 12 hours the reaction mixture is poured into a mixture of hexane and 1N hydrochloric acid. The reaction mixture is extracted several additional times with hexane and the combined organic extracts are washed 3 times with water and once with saturated sodium chloride and dried over sodium sulfate, filtered and evaporated. The residual oil is distilled to provide 1-cyclopropyl-2-butanone, b.p. 57°–60° C.

To 1 part by volume of magnesium in 25 parts by volume of tetrahydrofuran under argon is added a small amount of propargyl bromide and mercuric chloride to initiate a reaction. Once the reaction is started 6.3 parts of propargyl bromide in 50 parts by volume of tetrahydrofuran is added dropwise so as to maintain reflux. Upon completion of the reaction, the reaction is cooled to room temperature and poured into a mixture of ether and 1N HCl. The reaction mixture is extracted twice with ether. The ether extracts are combined and washed 3 times with water and one time with saturated sodium chloride, dried over anhydrous sodium sulfate, filtered, and evaporated to provide a residual oil. The residual oil is distilled under high vacuum to provide 4-methyl-4-hydroxy-6-cyclopropyl-hex-1-yne.

To a solution of 1.1 part of this material in 10 parts by volume of dimethylformamide containing 1 part of imidazole is added 0.865 parts of trimethylsilyl chloride. The reaction mixture is poured into an ether water mixture, extracted with more ether and the organic layers are combined and washed with water and saturated sodium chloride. The solvent is removed and the residual oil is chromatographed on 5% ethyl acetate/- hexane to provide 4-methyl-4-trimethylsilyloxy-6-cyclopropyl-hex-1-yne. 0.577 parts of this material is reacted with 0.748 parts of tri-n-butyl tin hydride at 20° C. with hν light to provide a compound of the formula

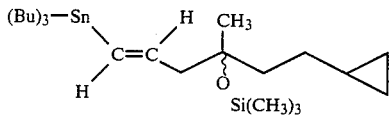

Starting with methyl-7(3-triethylsilyloxy-5-oxocyclopent-1-ene)-hept-4-cis-enoate and using the above vinyl stannane and following the procedures of Example 1, using equivalent quantities provides methyl 7[3α-hydroxy-2β-4-hydroxy-4-methyl-6-cyclopropyl-1-trans-hexenyl)-5-oxocyclopentane]1α-2-methyl-hept-4-cis-enoate having the formula

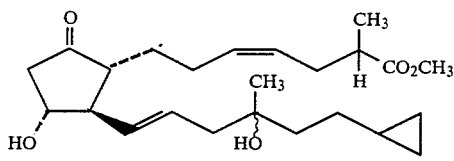

as a viscous oil, H¹ NMR δ1.12, d; δ3.65 s.

EXAMPLE 14

Hydrogenation of the product above in isopropanol at room temperature and atmospheric pressure with 5% palladium on carbon as catalyst provides methyl 7[3α-hydroxy-2β-4(RS)-4-hydroxy-4-methyl-6-cyclopropyl-hexan-5-oxocyclo-pentane]-1α-2-methyl-heptanoate having the formula

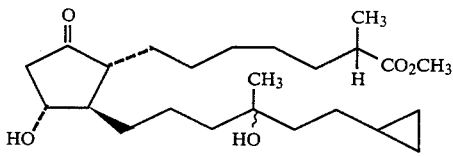

viscous oil, H¹ NMR δ1.14, δ4.15.

EXAMPLE 15

Substitution of 5-methyl-2-hexanone into Example 13 provides the vinyl sannane having the formula

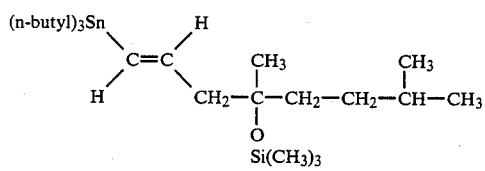

Starting with methyl 7-(3-triethylsilyloxy-5-oxocyclo-pent-1-ene-hept-4-cis-enoate and substituting the vinyl stannane above for trans-1-tri-n-butyl stannyl-4(RS)-trimethylsilyloxy-4-methyl-1-octene, and following the procedures of Example 1, using equivalent quantities provides methyl-7-(3α-hydroxy-2β-4-hydroxy-4,7-dimethyl-trans-octenyl)-5-oxocyclopentane]-1α-2-methyl-hept-4-cis-enoate having the formula

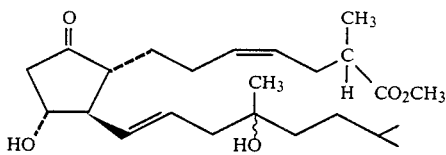

EXAMPLE 17

Hydrogenation of the product above in isopropanol at room temperature and atmospheric pressure with 5% palladium on carbon as catalyst provides methyl-7-[3α-hydroxy-2β-4(RS)-4,7-dimethyl-1-octan)-5-oxocyclopentane]-1α-2-methyl-heptanoate having the formula

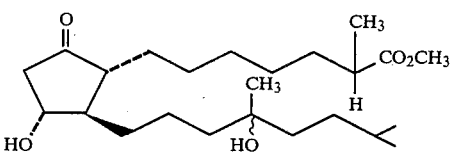

EXAMPLE 18

The 2-phenyl derivative is made according to the following reaction scheme

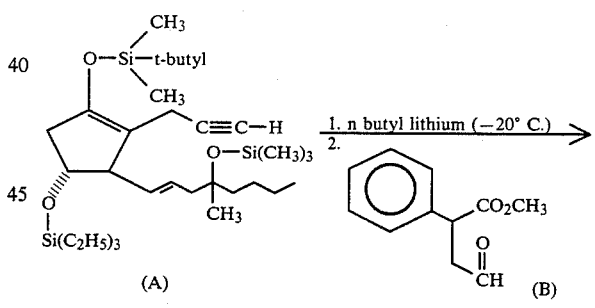

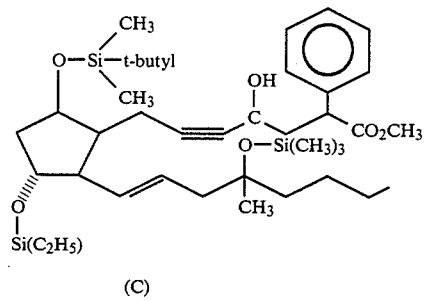

3. CH₃SO₂Cl
4. sodium iodide
5. tri-n-butyltin hydride
6. H₂, Pd/BaSO₄ catalyst

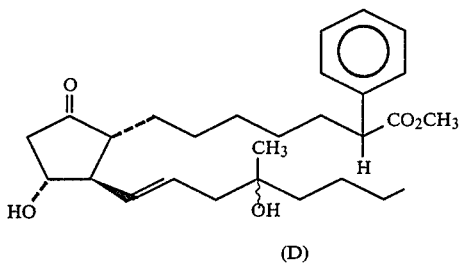

(D)

Precursor A is prepared as follows:

Propargyl magnesium bromide is prepared by adding a solution of propargyl bromide (as 145.5 parts of 80%, by weight, solution in toluene; in 150 parts by volume of diethyl ether to a slurry of 26 parts of iodine-activated magnesium and 0.34 parts of mercuric chloride in 450 parts by volume of ether. The rate of addition is adjusted to maintain a vigorous reflux. After addition is complete, the reaction mixture is stirred at room temperature for one hour and then cooled to 0°. A solution of 75 parts of 2-furancarboxaldehyde in 400 parts by volume of tetrahydrofuran is added dropwise, and the reaction mixture is stirred at room temperature for fifteen minutes, then poured onto a cold saturated ammonium chloride solution and stirred vigorously. The layers are separated and the aqueous layer is extracted with ether. The organic phase is washed with saturated ammonium chloride solution and with brine, dried over sodium sulfate, filtered, and concentrated to dryness. Distillation of the crude material at 1.0 torr gave 100.6 g of α-(2-propynyl)-2-furanmethanol, b.p. 68°–72°. Structure assignment is confirmed by the proton nmr spectrum.

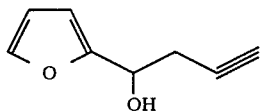

To a solution of 40.2 parts of this compound in 800 parts by volume of an 8:1 dioxane/water mixture is added 4 parts of p-toluenesulfonic acid. The reaction mixture is heated at 83° for 36 hours under argon, cooled, and diluted with 500 parts by volume of ethyl acetate. The organic phase is washed once with water and two times each with 5% sodium bicarbonate solution and brine solution. The aqueous washes are combined and extracted with ethyl acetate. The combined organic phases are dried over sodium sulfate, filtered and concentrated. Chromatography of the combined crude materials on silica gel (using 25% ethyl acetate in hexane as eluent) give 12.45 parts of the intermediate compound 4-hydroxy-5-(2-propynyl)-2-cyclopenten-1-one as a viscous oil. Structure assignment is confirmed by the proton nmr spectrum.

A solution of 14.5 parts of the cyclopentenone intermediate in 50 parts by volume of ether is poured into a column packed with 282 parts by volume of Grade III alumina (6% water by weight). The column is closed and allowed to stand at room temperature for twenty-four hours. The product is eluted from the column with ether and ethyl acetate to give 7.3 parts of 4-hydroxy-20 (2-propynyl)-2-cyclopenten-1-one) having the following formula

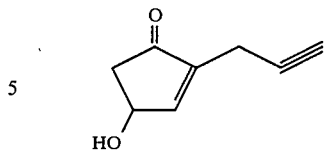

A solution of 0.250 parts of this compound in 4 parts by volume of dimethylformamide is treated successively with 0.200 parts of imidazole and 0.300 parts of triethylsilyl chloride. After stirring for thirty minutes, the reaction mixture is diluted with ether, washed with water, dried over sodium sulfate, filtered, and concentrated to dryness. The crude material is chromatographed on silica gel to provide 2-(2-propynyl)-4-[(triethylsilyl-oxy]-2-cyclopenten-1-one. Structure assignment is confirmed by the proton nmr spectrum.

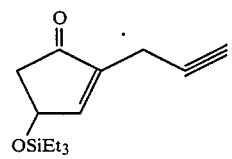

A solution of 10 parts trans-1-tri-n-butylstannyl-4(RS)-4-tri-methylsilyloxy-4-methyl-1-octene of Example 1 in 25 parts by volume of tetrahydrofuran is cooled to −60° under an argon atmosphere, and 11.8 parts by volume of 1 1.7M solution of n-butyllithium in hexane is added. The reaction mixture is stirred for forty-five minutes to which a solution of 2.62 parts of copper-1-pentyne and 6.4 parts of hexamethylphosphorus triamide in 75 ml of ether is added dropwise. After ten minutes, a solution of 2.4 parts of 2-(2-propynyl)-4-[(triethylsilyloxy]-2-cyclopenten-1-one in 20 parts by volume of ether is added, and the reaction mixture is stirred an additional 45 minutes. A solution of 3 parts of t-butyldimethylsilyl chloride in 15 parts by volume of ether is added, followed by the addition of 25 parts by volume of hexamethylphosphoric triamide. The temperature is allowed to rise to −20°, where it is maintained for one hour. The reaction mixture is poured into 1N hydrochloric acid and ether. The layers are separated and the organic phase is washed with water, dried over sodium sulfate, filtered and concentrated to dryness. The crude material is chromatographed on silica gel to give 4 parts of (1,1-dimethylethyl)dimethyl[3β-[4-methyl-4-[(trimethylsilyl)oxy]-1-cyclopenten-1-yl]oxy]silane as a viscous oil. Structure assignment is confirmed by the proton nmr spectrum.

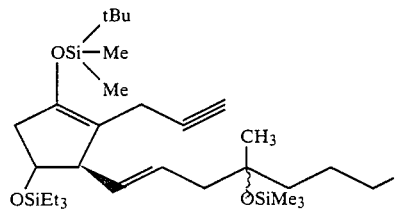

Precursor B is prepared as follows:

To a cold (−70° C.) solution of 2.22 parts of dimethyl-2-phenylsuccinate in 20 parts by volume of anhydrous tetrahydrofuran is added dropwise 10 parts by volume of 1 molar di-isobutyl aluminum hydride in toluene. The reaction is stirred at −70° C. for 2 hours. This reaction is then quenched by the addition of 1 parts by volume of methanol and the 1N hydrochloric acid until there is no longer a precipitate of aluminum salts. Ethyl ether is added, the layers are separated and the aqueous solution is extracted two more times with ether and the extracts are combined and washed with saturated sodium chloride and dried over anhydrous sodium sulfate. The resulting solution is filtered, the filtrate removed by evaporation under reduced pressure and the residual oil is chromatographed on silica gel using ethyl acetate/hexane to elute 3-carboxymethyl-3-phenyl propionaldehyde (Precursor B).

A solution of 0.578 parts of Precursor A in 10 parts by volume of anhydrous tetrahydrofuran containing a trace of triphenylmethyl chloride is cooled to −20° with stirring under an argon atmosphere. A solution of 0.69 parts by volume of 1.6 molar n-butyl lithium in hexane is added dropwise until the red color of the trityl anion is observed. The solution is stirred for 5 minutes, cooled to −70° C. and a solution of 0.576 parts of 3-carboxymethyl-3-phenylpropionaldehyde (Precursor B) in 4 parts by volume of tetrahydrofuran is added. The reaction is stirred for 90 minutes at −70° C., poured into water and ethyl ether. The mixture is mixed by shaking, the layers separated, and the aqueous layer is separated and extracted twice with ether and the ether extracts are combined, washed with saturated sodium chloride and dried over anhydrous sodium sulfate.

This solution is filtered, the ether removed by evaporation under reduced pressure, and the residual oil is chromotographed on silica gel using ethylacetate/hexane to provide Precursor C in the above reaction scheme.

To a cold (0° C.) stirred solution of 0.766 parts of C in 7 parts by volume of pyridine is added 0.230 parts of mesyl chloride. After 2 hours at 0° C., the reaction is complete. The reaction mixture is poured into water and extracted three times with ethyl ether. The combined ether layers are washed three times with saturated sodium chloride solution and dried over anhydrous sodium sulfate. This solution is filtered and the solvent is removed by evaporation at reduced pressure to provide a light yellow oil containing pyridine. The pyridine is removed in a nitrogen stream, to provide essentially pure mesylate derivative of C.

A solution of 0.862 parts of the mesylate and 0.525 parts of sodium iodide in 20 parts by volume of acetone is refluxed under nitrogen for 90 minutes. The acetone is removed by evaporation at reduced pressure and the residue is dissolved in an ether water mixture and shaken. The ether layer is separated, washed twice with water, once with saturated sodium chloride, twice with 2% sodium thiosulfate solution, twice with water and dried over anhydrous sodium sulfate. The solution is filtered, the solvent is evaporated at reduced pressure to provide a residual oil which is chromatographed on silica gel using ethyl acetate/hexane mixtures as eluent to provide the iodide derivative of C.

A solution of 0.867 parts of this iodide is reacted with 0.873 parts of tri-n-butyltin hydride and 0.040 parts of bis-azoisobutyronitrile in 22 parts by volume of benzene and refluxed with stirring under argon for one hour. The solvent is removed by evaporation at reduced pressure to provide a residual oil which is chromatographed on silica gel using hexane/ethyl acetate mixtures to provide a derivative of C where the hydroxyl group is replaced with hydrogen.

A solution of 0.2 parts in 10 parts by volume of a 3:1:1 acetic acid:tetrahydrofuran:water mixture is stirred at room temperature for 20 hours. The reaction is poured into ice water and extracted three times with ethyl ether. The ether layers are combined, washed with saturated sodium chloride and dried over anhydrous sodium sulfate. This solution is filtered and the solvent removed by evaporation under reduced pressure. The residual oil is azeotroped with toluene to remove acetic acid. The residue is chromatographed on silica gel using mixtures of ethyl acetate and hexane to provide a compound of the formula

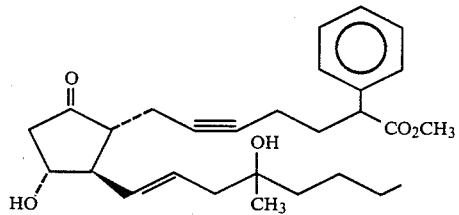

This compound is hydrogenated at room temperature and atmospheric pressure in toluene using palladium on barium sulfate as catalyst. The catalyst is removed by filtration, and the solvent removed by evaporation at reduced pressure. The residual oil is chromatographed on silica gel using mixtures of ethyl acetate and hexane as eluent to provide methyl 7-[3α-hydroxy-2β-4(RS)-4-hydroxy-4-methyl-1-trans-octenyl-5-oxocyclopentane]-1α-2-phenyl heptanoate having the formula

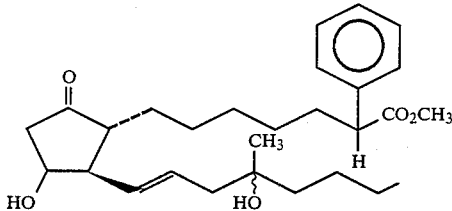

In a similar manner halo such as chloro and fluoro, trifluoromethyl, lower alkoxy such as methoxy and ethoxy and lower alkyl such as methyl, ethyl, isopropyl substituted phenyl and pyridyl derivatives are prepared.

What is claimed is:

1. A compound which is methyl 7-[3α-hydroxy-2β-4(RS)-4-hydroxy-4-methyl-1-trans-octenyl)-5-oxocyclopentane]-1α-2-allyl heptanoate.

2. A compound which is methyl 7-[3α-hydroxy-2β-4(RS)-4-hydroxy-4-methyl-1-trans-octenyl)-5-oxocyclopentane]-1α-2-benzyl-heptanoate.

3. A compound which is methyl 7-[3α-hydroxy-2β-4(RS)-4-hydroxy-4-methyl-1-trans-octenyl)-5-oxocyclopentane]-1α-2-cyclopentyl heptanoate.

4. A compound which is methyl 7-[3α-hydroxy-2β-4(RS)-4-hydroxy-4-methyl-1-trans-octenyl)-5-oxocyclopentane]-1α-2-iodo-heptanoate.

5. A compound which is ethyl 7-[3α-hydroxy-2β-4(RS)-4-hydroxy-4-methyl-1-trans-octenyl)-5-oxocyclopentane]-1α-2-fluoro-heptanoate.

6. A compound which is methyl 7-(3α-hydroxy-2β-4(RS)-4-hydroxy-4-methyl-1-trans-octenyl-5-oxocyclopentane]-1α-2-phenyl-heptanoate.

* * * * *